US011627925B2

United States Patent
Alhonnoro

(10) Patent No.: US 11,627,925 B2
(45) Date of Patent: Apr. 18, 2023

(54) X-RAY IMAGING SYSTEM AND METHOD FOR DENTAL X-RAY IMAGING

(71) Applicant: PaloDEx Group OY, Tuusula (FI)

(72) Inventor: Tuomas Alhonnoro, Espoo (FI)

(73) Assignee: PaloDEx Group OY, Tuusula (FI)

( * ) Notice: Subject to any disclaimer, the term of this patent is extended or adjusted under 35 U.S.C. 154(b) by 113 days.

(21) Appl. No.: 17/369,124

(22) Filed: Jul. 7, 2021

(65) Prior Publication Data
US 2022/0008025 A1 Jan. 13, 2022

(30) Foreign Application Priority Data

Jul. 8, 2020 (FI) ...................................... 20205736

(51) Int. Cl.
*A61B 6/14* (2006.01)
*G06T 7/80* (2017.01)
(Continued)

(52) U.S. Cl.
CPC ................ *A61B 6/14* (2013.01); *A61B 6/032* (2013.01); *A61B 6/4085* (2013.01);
(Continued)

(58) Field of Classification Search
CPC ........... A61B 6/14; A61B 6/032; A61B 6/501; A61B 6/145; A61B 34/10;
(Continued)

(56) References Cited

U.S. PATENT DOCUMENTS

| 2008/0137802 A1 | 6/2008 | Suzuki et al. |
| 2014/0355735 A1 | 12/2014 | Choi et al. |

(Continued)

FOREIGN PATENT DOCUMENTS

| EP | 3040028 A1 | 7/2016 |
| EP | 3117770 A1 | 1/2017 |

(Continued)

OTHER PUBLICATIONS

Finnish Patent Office Search Report for U.S. Appl. No. 20205736 dated Feb. 4, 2021 (2 pages).
(Continued)

*Primary Examiner* — Don K Wong
(74) *Attorney, Agent, or Firm* — Michael Best & Friedrich LLP

(57) ABSTRACT

The application relates to an X-ray imaging system (100) for dental X-ray imaging. The system comprises a controller, a rotating gantry (120), an X-ray source (124) for emitting X-rays, and an X-ray imaging detector (126) for receiving the X-rays from the source. The gantry comprises the source and detector (124, 126). The controller is configured to control the source to emit X-ray radiation and the detector for receiving the emitted radiation in order to acquire an X-ray image data. The system further comprises a depth information-producing camera (177), which is configured to produce a depth information, and a position information-producing component (183), which is configured to produce a position information, for acquiring at least a location data of the depth information-producing camera and detector during the irradiation, synchronously with the image data to be reconstructed.

19 Claims, 3 Drawing Sheets

(51) Int. Cl.
*G06T 7/50* (2017.01)
*A61B 6/03* (2006.01)
*A61B 6/00* (2006.01)
*G06T 11/00* (2006.01)

(52) U.S. Cl.
CPC .............. *A61B 6/4435* (2013.01); *A61B 6/54* (2013.01); *A61B 6/589* (2013.01); *G06T 7/50* (2017.01); *G06T 7/80* (2017.01); *G06T 11/005* (2013.01); *G06T 2207/10028* (2013.01)

(58) Field of Classification Search
CPC ........ A61B 2034/105; A61B 2034/107; A61B 2034/2065; A61B 2090/367; A61B 2090/373; A61B 6/12; A61B 6/4417; A61B 6/4266; A61B 6/547; A61B 6/584; A61B 2090/3762; A61B 1/24; A61B 2034/2057; A61B 5/0077; A61B 8/5261; G01T 1/249; G01T 1/1648; G06T 3307/10116; G06T 2207/30036; G06T 2007/10028; G06T 7/30; G06T 15/00
See application file for complete search history.

(56) References Cited

U.S. PATENT DOCUMENTS

2016/0256123 A1  9/2016  Lu et al.
2017/0135655 A1  5/2017  Wang et al.
2019/0343478 A1  11/2019  Sorensen et al.

FOREIGN PATENT DOCUMENTS

| | | | |
|---|---|---|---|
| EP | 3146900 A1 | 3/2017 | |
| EP | 3527139 A1 | 8/2019 | |
| EP | 3673806 A2 | 7/2020 | |
| JP | 2019171020 A | * 10/2019 | ............. A61B 6/032 |
| WO | 2011095694 A1 | 8/2011 | |
| WO | 2018122451 A1 | 7/2018 | |

OTHER PUBLICATIONS

European Patent Office Search Report for Application No. 21184227.3 dated Nov. 29, 2021 (2 pages).

* cited by examiner

X-RAY IMAGING SYSTEM AND METHOD FOR DENTAL X-RAY IMAGING

TECHNICAL FIELD

The application relates generally to an X-ray imaging system and an X-ray imaging method for dental X-ray imaging.

BACKGROUND

Known dental X-ray imaging systems, which are used in computed tomography (CT) X-ray imaging, require that a patient to be imaged is positioned between an X-ray source and an X-ray detector, whereupon it is possible to irradiate the patient by means of the X-ray source and to receive penetrated radiation by means of the X-ray detector. The received radiation is converted into a form of X-ray image data in the X-ray detector and this image data is then used in the reconstruction of three-dimensional (3D) CT volume from the patient.

The positioned patient is supported to an imaging position during the X-ray exposure by means of head supporters. The supporting is carried out in order to keep the patient still as long as the exposure lasts. The supporters comprise a lower shelf, which supports a tip of patient's chin, and a temple support, which supports a patient's temple.

The positioning and supporting of patient is the most time consuming task in the imaging and, regardless of how correctly and carefully the patient has been supported, it is difficult to prevent an undesirable movement of patient entirely during the exposure. The existing movement of patient causes image artefacts across reconstructed CT volumes, e.g., round objects may produce sharp corners or become elliptic, sharp features become blurry, and beam hardening artefacts get exaggerated.

SUMMARY

One object of the invention is to withdraw drawbacks of known solutions and to provide an X-ray imaging system, which enables a simultaneous localization of the X-ray source and detector geometry in a moving patient coordinate system during an exposure of patient, an X-ray exposure without any support for patient's head, indirect geometry calibration, and a continuous tracking of geometry calibration drifting with respect to the system or environment.

One object of the invention is fulfilled by providing the imaging system, imaging method, computer program, and computer-readable medium according to the independent claims.

Embodiments of the invention are specified by the imaging system, imaging method, computer program, and computer-readable medium according to the independent claims.

An X-ray imaging system for dental X-ray imaging comprises a controller, a rotating gantry, an X-ray source for emitting X-rays, and an X-ray imaging detector for receiving the X-rays from the source. The gantry comprises the source and detector. The controller is configured to control the source to emit X-ray radiation and the detector for receiving the emitted radiation in order to acquire an X-ray image data. The system further comprises a depth information-producing camera, which is configured to produce a depth information, and a position information-producing component, which is configured to produce a position information, for acquiring at least a location data of the depth information-producing camera and detector during the irradiation, synchronously with the image data to be reconstructed.

An X-ray imaging method for dental X-ray imaging, which is performed by the previous X-ray imaging system, comprises a step of presenting the X-ray imaging system with the depth information-producing camera and the a position information-producing component. The method further comprises a step of controlling, by the controller of the system, the X-ray source and the X-ray detector in the rotating gantry in order to acquire the X-ray image data. The method further comprises a step of acquiring, by the depth information-producing camera together with the position information-producing component, at least the location data of the depth information-producing camera and detector during the acquisition of the image data, synchronously with the image data to be reconstructed.

A computer program that comprises instructions, which, when the program is executed by a computer, which is in accordance with the previous X-ray imaging system, cause the computer to perform at least the steps of the previous X-ray imaging method.

A tangible, non-volatile computer-readable storage medium comprises the previous computer program.

BRIEF DESCRIPTION OF THE FIGURES

The exemplary embodiments of the invention are explained with reference to the following figures.

DETAILED DESCRIPTION OF THE FIGURES

Figure 1A:
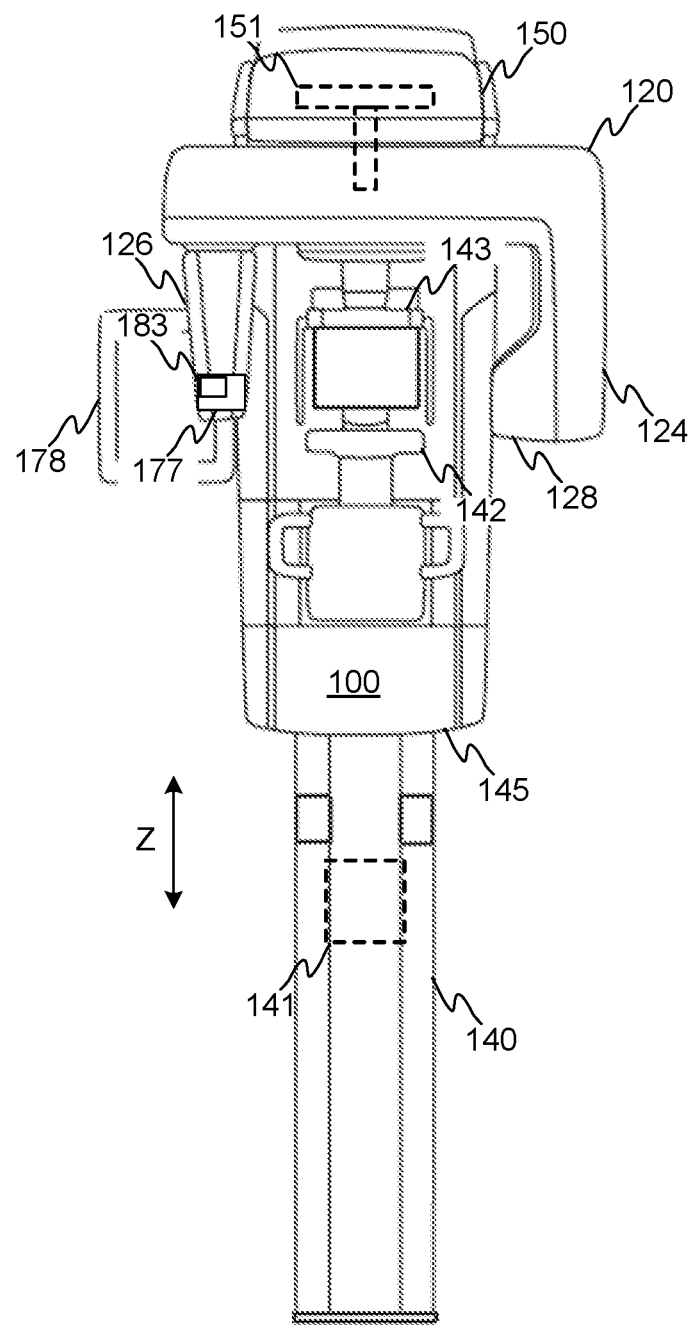
FIG. 1a presents an X-ray imaging system from the front

FIG. 1a presents an X-ray imaging system (unit) 100 for acquiring an image data from an object, e.g. a patient or calibration target, in dental X-ray imaging, e.g. in extraoral dental X-ray imaging. The acquired image data is used to form a two-dimensional (2D) X-ray image or to reconstruct a three-dimensional (3D) X-ray volume from at least part of imaged object.

The system 100 is used to perform at least Computed Tomography (CT) imaging, e.g. a cone-beam CT (CBCT) imaging or other type of CT imaging, which results (produces) the image data for the reconstruction of 3D volume from the imaged object. The system 100 may also be used to perform Panoramic imaging, which results the image data for the formation of Panoramic 2D image, as the system 100 presented in the figures. The system 100 may also be used to perform Cephalometric imaging, if the system 100 is equipped with parts, which are necessary for the Cephalometric imaging and result the image data for the formation of Cephalometric 2D image.

The system 100 comprises a rotating gantry (gantry part, rotator) 120 that embodies and supports an X-ray source (source part, head) 124 and an X-ray imaging detector (imaging detector part, head) 126, which are used in the acquisition of image data for at least the reconstruction of 3D volume. The source and detector 124, 126 may also be used in the acquisition of image data for the formation of Panoramic 2D image and Cephalometric 2D image, if necessary parts exist.

Figure 1B:
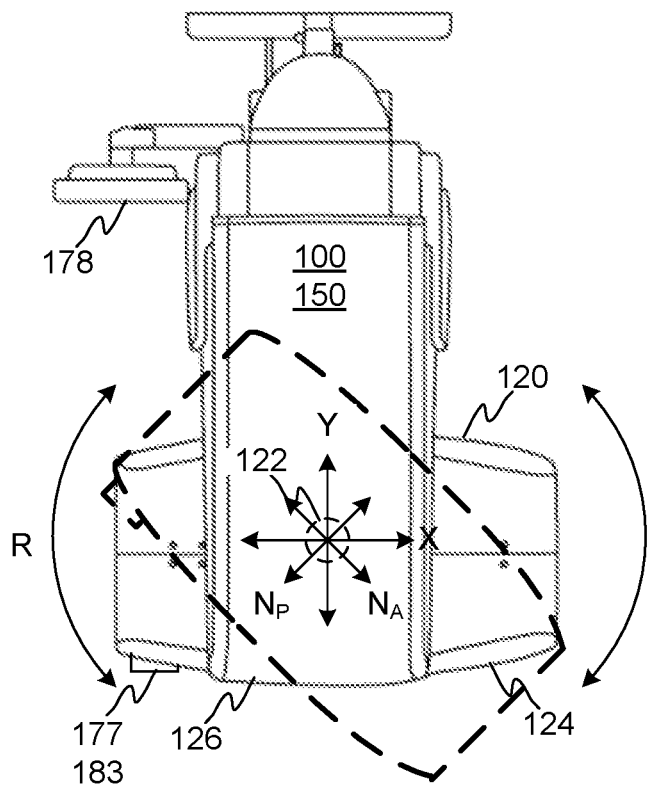
FIG. 1b presents the imaging system from above and imaging movements of its gantry

The gantry 120 may have a form of letter C, as presented in FIGS. 1a and 1b, whereupon the source 124 may be attached on one end of the gantry 120 and the detector 126 may be attached on the other end of the gantry 120 so that the source and detector 124, 126 are opposed from each other.

The source 124 comprises an X-ray source that emits X-rays, i.e. generates an X-ray beam, for at least the CT imaging, which may be the CBCT imaging, wherein the beam is a cone-shaped beam, or alternative CT imaging, wherein the beam is a pyramidal-shaped beam, half-moon-shaped cone beam, or other shaped beam. The source 124 may be used also in the Panoramic imaging.

The detector 126 comprises at least one X-ray detector, e.g. one or two X-ray detectors, that receives the emitted X-rays (the beam) from the source 124 and generates the image data from the X-ray exposed, i.e. imaged, object. The received image data is used in the formation of Panoramic image or the reconstruction of 3D volume from the object.

A one-sensor (single-sensor) detector 126 comprises a Panoramic/CT combination sensor, a Panoramic/CT/Cephalometric combination sensor, or a Panoramic/CT sensor, which enables also one-shot Cephalometric imaging. The one-sensor detector 126 may be adjustable so that it is possible to rotate and/or to move the sensor (detector 126) relative to the gantry 120 in order to position it preferably perpendicularly (towards) to the source 124.

A two-sensors detector 126 may comprise a Panoramic sensor and a CT sensor, or a Cephalometric sensor, which enables also Panoramic imaging, and a CT sensor. The two-sensors detector 126 may be adjustable so that there are several ways to attach the sensors and it is possible to change a sensor that locates within the beam. A used sensor is positioned preferably perpendicularly to the source 124.

Alternatively, the detector 126 can be fixed.

The gantry 120 also comprises a collimator (collimator part, X-ray beam limiting) 128 for the source 124 that collimates the beam from the source 124. The collimator 128 may be attached in front of the source 124 and it controls a size and shape of the beam during the imaging so that the beam matches needs of a selected imaging mode (protocol), e.g. the CT or Panoramic imaging mode, selected image size, and related sensor size.

The system 100 also comprises a column (column part) 140 that supports the system 100, and adapts its height Z and, simultaneously, a height of the gantry 120 to a height of object for the CT or Panoramic imaging.

The system 100 may comprise a carriage (carriage part) 145 that forms a structure, which may provide an up/down Z-movement and a support for other parts that are adapted to be moved at the same time.

The column 140 comprises height adapter (adapting part) 141 that causes the up/down Z-movement for the carriage 145, if the system 100 comprises the carriage 145. The adapter 141 may comprise e.g. a height motor, a gear, a threaded rod, and telescopic or counterweighted part that realizes the Z-movement as a telescopic or counterweighted movement. The height motor drives the other parts of adapter 141 for adapting a height of the carriage 145.

The system 100 may also comprise a patient supporter (support part) 142, 143 that is used for supporting the object in the CT or Panoramic imaging, as presented in FIGS. 1*a* and 1*b*, but not necessarily. The patient supporter 142, 143 may comprise a lower shelf 142, which is attached to the carriage 145, and a temple support 143. The lower shelf 142 may support a tip of a chin of object and the temple support 143 may support a forehead or temple of object.

The system 100 also comprises an upper shelf 150 that supports the gantry 120 and permits the gantry 120 to move with respect to the upper shelf 150. The upper shelf 150 may be attached to the carriage 145 by a fixed joint.

The gantry 120 may be attached to the upper shelf 150 with an attacher (attaching part) 151 that allows the gantry 120 to rotate around its rotation axis 122 and to move with respect to the upper shelf 150.

The carriage 145 may comprise the lower shelf 142, the temple support 143, the upper shelf 150, and the gantry 120, whereupon, when the height adapter 141 realizes the Z-movement, height adapter 141 adapts the height of the parts 142, 143, 150, 120.

The system 100 120 also comprises a camera (camera part) 177, which is capable of producing a depth information. The depth-sensing camera 177 may comprise an optical camera, e.g. a color or monochrome camera, and a depth camera, e.g. an infrared (I R) camera, whereupon the optical camera or the depth camera functions as a main camera. Alternatively, the camera 177 may comprise two optical cameras, e.g. two color or monochrome cameras, whereupon one of optical cameras functions as a main camera. Alternatively, the camera 177 may comprise a time-of-flight (ToF) camera. The camera 177 may be attached to the gantry 120 so that at least its main optical camera is installed in connection with the detector 126. Other camera, i.e. the depth camera and non-main optical camera in the alternatives may also be installed in connection with the gantry 120, e.g. with the detector 126, or with other part of the system 100, e.g. the column 140 or the carriage 145, if such exists.

The system 100 also comprises a position information-producing component 183, which capable of determining a location of at least the main camera of camera 177, i.e. it is capable of producing a location data of at least the main camera of camera 177. The position information-producing component 183 may be e.g. an inertial measurer (IMU). The position information-producing component 183 may be installed e.g. in the gantry 120 as presented in FIGS. 1*a* and 1*b*, or in the column 140 of the carriage 145, if such exists.

FIG. 1*b* presents how the attacher 151 allows a rotational movement (R-movement) for the gantry 120 so that the gantry 120 can rotate up to 400 degrees around its rotation axis 122. This R-movement may be used for the CT imaging, Panoramic imaging, or both imaging modes.

The attacher 151 may also allow a first linear Y-movement for the gantry 120 so that its rotation axis 122 and, thus, its rotation center may be adjusted (positioned) along the Y-movement with respect to the upper shelf 150 before imaging (scan) movements of imaging and during the imaging (imaging movements with or without irradiation). The Y-movement is parallel to the upper shelf 150.

The attacher 151 may also allow a second linear X-movement so that the rotation axis 122 can be adjusted within a plane defined by the X- and Y-movements before the imaging movements of the imaging and during the imaging. The X-movement is perpendicular to the Y-movement.

The attacher 151 may also allow a third $N_A$-movement, which moves the rotation axis 122 in respect to the gantry 120. The $N_A$-movement of the rotation axis 122 along the beam may be used to change a magnification within the CT and Panoramic imaging modes.

The attacher 151 may also allow a fourth $N_P$-movement, which moves the rotation axis 122 perpendicular to the beam. It may be used to a change between offset imaging and symmetrical imaging in the CT imaging, whereupon that affects to a Field Of View (FOV).

Alternatively, instead of presented fixed joint in FIGS. 1*a* and 1*b*, the upper shelf 150 may be attached to the column 140, or carriage 145 if such exists, by a pivot joint (not presented), which enables a pivot movement of upper shelf 150 around the column 140 (carriage 145) and with respect to the patient supporter 142, 143, if such exists, so that the gantry 120 is over e.g. a position to which a patient to be imaged will be positioned (patient supporter 142, 143).

In this alternative embodiment of system 100, the attacher 151 also allows the previously explained rotational R- and linear movements for the gantry 120 so that the gantry 120 can rotate up to 400 degrees around its rotation axis 122, and the gantry 120 can move linearly with respect to the upper shelf 150 e.g. parallelly or in a certain angle with respect to the parallel direction.

In this alternative embodiment of system 100, attacher 151 is able to move at least one linear movement so that the rotation axis 212 and, thus, the rotation center with respect to the upper shelf 150 can be adjusted along the linear movement. This way the rotation axis 122 can be positioned within a plane defined by the pivot movement of the upper shelf 150 and the linear movement(s) of the rotating gantry 120 during the imaging.

The movements and necessary components of alternative embodiment of system 100 have been presented more accurately in published patent application FI 20145617.

The system 100 also comprises a rotating motor (not presented) that rotates and/or moves the gantry 120 as explained previously by the attacher 151 during its positioning with respect to the lower shelf 142 so that the gantry 120 is over the lower shelf 142, and/or during imaging. The rotating motor may be in the gantry 120 or in the upper shelf 150.

The system 100 may comprise a first moving motor that moves the collimator 128 and/or the detector 126 during positioning of the gantry 120 and/or during the imaging. The first moving motor may be in the gantry part 120 or the upper shelf 150.

The system 100 may use the R-movement and read out the CT detector during a imaging phase of CT imaging resulting the image data for the 3D volume. The system 100 may also use the X and/or Y-movements during the imaging phase of CT imaging.

The system 100 may produce projection X-ray images of Region Of Interest (ROI) so that a center of ROI and the R-movement coincide. An effective rotation angle (aperture) may be appr. 180-360 degrees depending on the system 100.

The system 100 may use at least one movement of the R-, X-, and Y-movements during an imaging phase of Panoramic imaging resulting the image data for the Panoramic image.

If the upper shelf 150 is attached by the pivot joint as previously explained, the system 100 may use at least one movement of R-, pivot, linear movements during the imaging phase of CT and Panoramic imaging.

Figure 2:
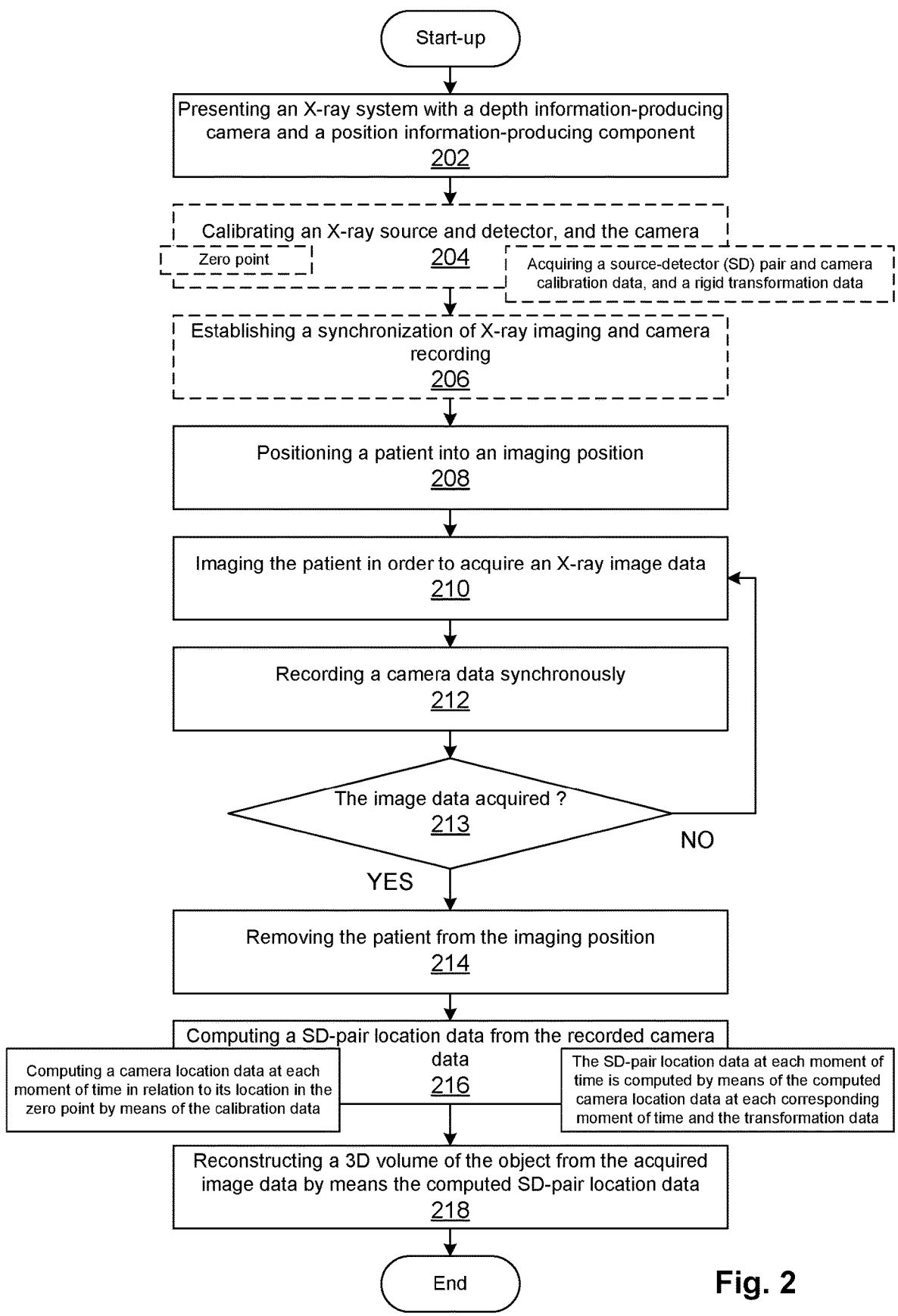
FIG. 2 presents a flowchart of X-ray imaging method

FIG. 2 presents an X-ray imaging method 201, e.g. in the CT imaging which is performed by means of the system 100, which explained in context of the previous figures.

At step 202, the system 100 presents the source 124, detector 126, camera 177, and position information-producing component 183. An operator of system 100 starts the system 100, whereupon the system 100 initializes itself in order to acquire an image data from the source 126, a camera data from the camera 177, and a location data from position information-producing component 183, which are used in a calibration of parts 124, 126, 177 and a reconstruction of 3D volume of imaged object.

At step 204, the operator instructs a controller (control part) 370 of system 100, by means of its user interface (UI, user interface part) 178, after detecting a need for calibration on the grounds of at least one predetermined condition, e.g. a certain parameter describing a condition of system 100, a certain elapsed time after the previous calibration, or a number of performed imaging processes, which exceeds a predetermined limit, to perform the calibration of source, detector, and camera 124, 126, 177 in order to acquire a source-detector (SD) pair calibration data, camera calibration data, and a rigid (joint) transformation data between the SD pair 124, 126 and camera 177. Alternatively, the controller 370 may initiavely (automatically) detect the need for calibration when at least one previously explained condition exceeds a predetermined limit value and to perform the calibration of source, detector, and camera 124, 126, 177.

The system 100 calibrates the SD pair 124, 126 by e.g. imaging (scanning) the calibration target to map the target into its 3D space (CT space) and, at the same time, the camera 177 to which the target is jointly visible by imaging the target to map the calibration target in its local 3D space (camera space). At the same time, in this so-called zero point, the controller 370 acquires, by means of the camera 177 and the position information-producing component 183, the transformation data, which basis on an established geometry between the source, detector, and camera 124, 126, 177.

At step 206, the operator instructs the controller 370, by means of the UI 178 to synchronize the acquisition of image data, i.e. the imaging of patient, which is performed by means of the source and detector 124, 126; the recording of camera data, and the acquisition of location data, which is performed by means of the position information-producing component 183. As a result of this step 206, the acquisitions of image and location data, and the recording of camera data are performed synchronously.

The steps 204 and 206 are not necessary to perform every time but these steps 204, 206 may be performed automatically or operator-initially quite rarely when comparing to known calibration solutions.

At step 208, the operator instructs a patient, i.e. an object, to position or positions the patient between the source and detector 124, 126 so that it is possible to image the patient. The patient may be positioned by means of the patient supporter 142, 143 so that the lower shelf 142 supports a tip of a chin of patient, the temple support 143 supports a forehead or temple of patient, or all parts of patients supporter 142, 143 support the patient. Alternatively, the patient may be positioned freely, without the aid of patient supporter 142, 143 between the source and detector 124, 126.

At step 210, the operator instructs the controller 370, by means of the UI 178, to control the system 100 to perform necessary imaging movements, by means of a mover (movement part) 375, and during these movements, the source 124 to emit X-ray radiation and the detector 126 to receive the emitted radiation in order to acquire the image data from the positioned patient.

At step 212, at the same, i.e. during the acquisition of image data, and synchronously with the acquisition of image data, the camera 177 images the source 124, the positioned patient, or both in order to acquire the camera data and the position information-producing component 183 determines a location data so that it tracks the location of the camera 177 with respect to the imaging object, e.g. the positioned patient, during the acquisition of the camera data.

At step 213, if all imaging and recording has not been completed, the method returns back to step 210. Otherwise, when all necessary data has been acquired, the method 201 continues to next step 214.

At step 214, after the acquisition of necessary image data has been completed, the operator instructs the patient to exit from the imaging position.

At step 216, the controller 370 computes a location data of SD pair 124, 126 from the recorded camera data by computing a location data of camera 177 at each moment of time in relation to the location of camera 177 during the calibration in the zero point by means of the calibration data of camera 177 and by using the computed location data of camera 177 at each moment of time and the transformation data to compute the location data of SD pair 124, 126 at the each moment of time.

At step 218, the controller 370 uses the computed location data of SD pair 124, 126 at the each moment of time when reconstructing the acquired image data to a 3D volume from the imaged patient.

Figure 3:
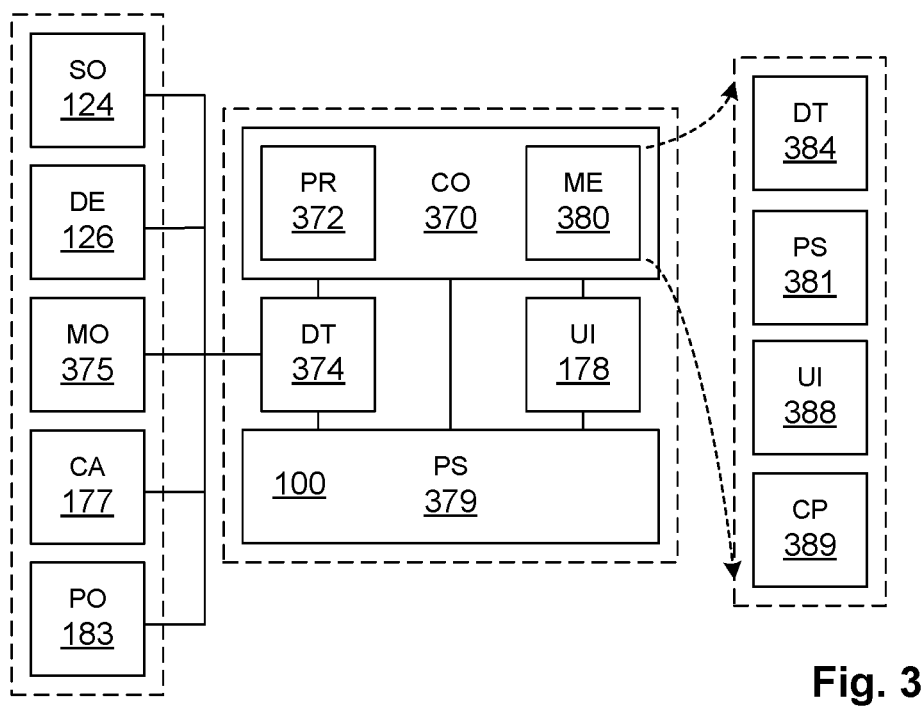
FIG. 3 presents parts of the imaging system

FIG. 3 presents the system 100 that is able to acquire an X-ray image data and a camera data, which are used in a reconstruction of 3D volume.

The system 100 comprises the controller 370 that controls the operations and movements of e.g. its parts 120, 124, 126, 128, 141, 150, 151, 177, 178, 183, 374, 375, 379 so that the system 100 operates as explained in context of the previous figures.

The controller 370 comprises a processor (processor part) 372 that performs an operator (user)-initiated and/or computer program (software)-initiated instructions, and processes data in order to run applications. The processor 372 may comprise at least one processor, e.g. one, two, three, or more processors.

In the case, where the processor 372 comprises several processors, the processors 372 may locate merely in the system 100 or in at least one separate device, or so that one part of the processors 372 locates in the system 100 and another part of the processors 372 locates in the at least one separate device, which is able to perform the reconstruction of 3D volume and the formation of 2D image from the imaged object.

The controller 370 also comprises a memory (memory part) 380 that stores and maintains data. The data may be instructions, computer programs, and data files. The memory 380 comprises at least one memory, e.g. one, two, three, or more memories.

The system 100 also comprises the data transferer (data transfer part) 374 of which the controller 370 uses to send control commands, data requests, and data to at least one of parts 124, 126, 128, 141, 177, 178, 183, 375, 379, e.g. the source 124, detector 126, mover 375, camera 177, or position information-producing component 183, in the system 100. The data transferer 374 also receives, in the control of controller 370, control commands, data requests, and data from at least one of parts 124, 126, 128, 141, 177, 178, 183, 375, 379, e.g. the source 124, detector 126, mover 375, camera 177, or position information-producing component 183. The communication between the data transferer 374 and the parts 124, 126, 128, 141, 177, 178, 183, 375, 379 in the system 100 is provided through a wired and/or wireless connection(s).

The mover 375 comprises motors, drivers, or other parts, of which the controller 370 uses to cause the movements of at least one of parts 120, 124, 126, 128, 141, 150, 151.

The system 100 also comprises the camera 177 of which the controller 370 uses to obtain the camera data and the position information-producing component 183 of which the controller uses to obtain the position data as explained in context of the previous figures.

The system 100 also comprises the UI 178, which enables for the operator to input control commands, to receive information and/or instructions, and to display information. The UI 178 may comprise at least one of a touchscreen, at least one function key, and a wired or wireless remote controller. The UI 178 may be attached to the column 140 or to carriage 145 as presented in FIGS. 1a and 1b.

The system 100 also comprises a power supply (power supply part) 379, which enables to power the system 100. The power supply 379 comprises at least one component for powering the system 100, e.g. a connection to electric plugs, battery, or regulator.

The memory 380 stores at least a data transfer application 384 for operating (controlling) the data transfer part 374, a user interface (UI) application 388 for operating the UI 178, and a power supply application 381 for operating the power supply 379.

The memory 380 also stores a computer program (computer software, computer application) 389, which uses at least one of parts 124, 126, 128, 141, 151, 177, 183, 375 in order to control the operations of system 100 as explained previously in this description and figures, when run in a computer, eg. in the system 100, by means of controller 370.

The computer program 389, i.e. its computer program code, may be stored in a tangible, non-volatile (non-transitory) computer-readable medium, e.g. a Compact disc (CD) or Universal Serial Bus (USB) storage device.

The invention and its several advantages have been now explained with reference to the previous exemplary embodiments. It is clear that the invention is not only restricted to these embodiments, but it comprises all possible embodiments within the scope of the following claims.

The invention claimed is:

1. An X-ray imaging system for dental X-ray imaging, comprising
   a controller,
   a rotating gantry,
   an X-ray source for emitting X-rays, and
   an X-ray imaging detector for receiving the X-rays from the source,
   wherein the gantry comprises the source and detector,
   wherein the controller is configured to control the source to emit X-ray radiation and the detector for receiving the emitted radiation in order to acquire an X-ray image data, and
   wherein the system further comprises a depth information-producing camera, which is configured to produce a depth information, and a position information-producing component, which is configured to produce a position information, for acquiring at least a location data of the depth information-producing camera and detector during the irradiation, synchronously with the image data to be reconstructed.

2. The system according to claim 1, wherein the depth information-producing camera comprises optical and depth cameras, or two optical cameras, and one of the cameras belonging to the depth information-producing camera functions as a main camera.

3. The system according to claim 2, wherein the position information-producing component is configured to determine a position of at least the main camera of the depth information-producing camera.

4. The system according to claim 2, wherein the depth information-producing camera is attached to the gantry so that at least the main camera is installed in connection with the detector.

5. The system according to claim 2, wherein the controller controls the depth information-producing camera to record a camera data synchronously with the acquisition of the image data during the irradiation.

6. The system according to claim 5, wherein the controller controls a calibration of the depth information-producing camera and the source in order to acquire a calibration data of the depth information-producing camera and the source before the irradiation.

7. The system according to claim 6, wherein the controller acquires a rigid transformation data on a grounds of an established geometry between the depth information-producing camera, source, and detector.

8. The system according to claim 7, wherein the controller computes the source-detector location data from the recorded camera data by computing a location data of the depth information-producing camera at each moment of time in relation to the location of the depth information-producing camera during the calibration by means of the calibration data of the depth information-producing camera and by using the computed location data of the depth information-producing camera at each moment of time and the transformation data to compute the source-detector location data at the each moment of time.

9. The system according to claim 1, wherein the dental imaging is cone-beam computed tomography X-ray imaging.

10. The system according to claim 9, wherein the controller uses the computed source-detector location data at the each moment of time when reconstructing the acquired image data to a three-dimensional X-ray volume.

11. The system according to claim 1, wherein the controller controls a synchronization of the acquisition of the image data and the recording of the depth information-producing camera before the irradiation.

12. An X-ray imaging method for dental X-ray imaging by an X-ray imaging system, comprising steps of
presenting the X-ray imaging system with a depth information-producing camera and a position information-producing component,
controlling, by a controller of the system, an X-ray source and an X-ray detector in a rotating gantry in order to acquire X-ray image data, and
acquiring, by the depth information-producing camera together with the position information-producing component, location data of the depth information-producing camera and the X-ray detector during the acquisition of the image data, synchronously with the image data to be reconstructed.

13. A tangible, non-volatile computer-readable storage medium comprising a computer program including instructions, which, when executed by a computer, cause the computer to perform at least the steps of:
presenting an X-ray imaging system with a depth information-producing camera and a position information-producing component,
controlling, by a controller of the system, an X-ray source and an X-ray detector in a rotating gantry in order to acquire the X-ray image data, and
acquiring, by the depth information-producing camera together with the position information-producing component, the location data of the depth information-producing camera and detector during the acquisition of the image data, synchronously with the image data to be reconstructed.

14. The system according to claim 3, wherein the depth information-producing camera is attached to the gantry so that at least the main camera is installed in connection with the detector.

15. The system according to claim 3, wherein the controller controls the depth information-producing camera to record a camera data synchronously with the acquisition of the image data during the irradiation.

16. The system according to claim 4, wherein the controller controls the depth information-producing camera to record a camera data synchronously with the acquisition of the image data during the irradiation.

17. The system according to claim 2, wherein the controller controls a calibration of the depth information-producing camera and the source in order to acquire a calibration data of the depth information-producing camera and the source before the irradiation.

18. The system according to claim 3, wherein the controller controls a calibration of the depth information-producing camera and the source in order to acquire a calibration data of the depth information-producing camera and the source before the irradiation.

19. The system according to claim 4, wherein the controller controls a calibration of the depth information-producing camera and the source in order to acquire a calibration data of the depth information-producing camera and the source before the irradiation.

* * * * *